United States Patent
Wan et al.

(10) Patent No.: US 10,940,135 B2
(45) Date of Patent: Mar. 9, 2021

(54) PACLITAXEL PHARMACEUTICAL COMPOSITION AND PHARMACEUTICAL PREPARATION THEREOF, PREPARATION PROCESS AND USE THEREOF

(71) Applicant: Sinotherapeutics Inc., Shanghai (CN)

(72) Inventors: Jiansheng Wan, Shanghai (CN); Yun Fang, Shanghai (CN); Kun Li, Shanghai (CN)

(73) Assignee: SINOTHERAPEUTICS INC., Shanghai (CN)

(*) Notice: Subject to any disclaimer, the term of this patent is extended or adjusted under 35 U.S.C. 154(b) by 0 days.

(21) Appl. No.: 16/075,381

(22) PCT Filed: Feb. 3, 2017

(86) PCT No.: PCT/CN2017/072827
§ 371 (c)(1),
(2) Date: Aug. 3, 2018

(87) PCT Pub. No.: WO2017/133662
PCT Pub. Date: Aug. 10, 2017

(65) Prior Publication Data
US 2019/0038592 A1    Feb. 7, 2019

(30) Foreign Application Priority Data
Feb. 4, 2016    (CN) .......................... 201610080378.6

(51) Int. Cl.
| A61K 31/337 | (2006.01) |
| A61K 47/22  | (2006.01) |
| A61K 47/38  | (2006.01) |
| A61P 35/00  | (2006.01) |
| A61K 9/00   | (2006.01) |

(52) U.S. Cl.
CPC .......... *A61K 31/337* (2013.01); *A61K 9/0053* (2013.01); *A61K 47/22* (2013.01); *A61K 47/38* (2013.01); *A61P 35/00* (2018.01)

(58) Field of Classification Search
CPC ...... A61K 31/337; A61K 47/22; A61K 47/38; A61K 9/0053; A61P 35/00
See application file for complete search history.

(56) References Cited

U.S. PATENT DOCUMENTS

2017/0027931 A1    2/2017  Wan et al.

FOREIGN PATENT DOCUMENTS

| CN | 101380474 A    | 3/2009 |
| CN | 101836958 A  * | 9/2010 |
| CN | 101836958 A    | 9/2010 |
| CN | 103083240 A    | 5/2013 |
| CN | 103491964 A    | 1/2014 |
| CN | 104971045 A    | 10/2015 |
| EP | 2236130 A1     | 10/2010 |
| JP | 2009514884 A   | 4/2009 |
| WO | 020664132 A2   | 8/2002 |
| WO | 2007056205 A2  | 5/2007 |
| WO | 2012122279 A1  | 9/2012 |
| WO | 2013060304 A1  | 5/2013 |

OTHER PUBLICATIONS

International Search Report and Written Opinion dated May 8, 2017 in International Application No. PCT/CN2017/072827.
Wang et al., "Application Progress of Hot Melt Extrusion Technology in Field of Pharmaceutical Preparations," Chinese Journal of Experimental Traditional Medical Formulae, vol. 19, No. 23, pp. 327-334 (Dec. 2013) (First Page English Abstract).
Supplementary European Search Report dated Aug. 9, 2019 in EP 17746982.2.
Office Action dated Jul. 16, 2019 in JP 2018-520461 (with English translation).

* cited by examiner

*Primary Examiner* — Jean P Cornet
(74) *Attorney, Agent, or Firm* — Ice Miller LLP

(57) ABSTRACT

A paclitaxel pharmaceutic composition and a pharmaceutic preparation, a preparation process therefor and use thereof are provided. The paclitaxel composition contains paclitaxel as an active ingredient and hydroxypropyl methyl cellulose derivative as a carrier material. The paclitaxel preparation is in the form of an oral solid preparation. The paclitaxel composition and pharmaceutic preparation thereof can be used for the preparation of a drug for preventing and treating malignancies and relevant diseases in mammals.

9 Claims, 2 Drawing Sheets

PACLITAXEL PHARMACEUTICAL COMPOSITION AND PHARMACEUTICAL PREPARATION THEREOF, PREPARATION PROCESS AND USE THEREOF

CROSS-REFERENCE TO RELATED APPLICATION

This application is a Section 371 of International Application No. PCT/CN2017/072827, filed Feb. 3, 2017, which was published in the Chinese language on Aug. 10, 2017, under International Publication No. WO 2017/133662 A1, which claims priority under 35 U.S.C. § 119(b) to Chinese Patent Application No. 201610080378.6, filed on Feb. 4, 2016, the disclosures of which are incorporated herein by reference in their entireties.

TECHNICAL FIELD

Provided are a paclitaxel pharmaceutical composition and a pharmaceutical preparation thereof, preparation process and use thereof, in particular a pharmaceutical composition comprising paclitaxel as an active ingredient, as well as a pharmaceutical preparation comprising the pharmaceutical composition, preparation process thereof and use thereof.

BACKGROUND

Paclitaxel (PTX) is a natural alkaloid extracted from Taxus plants. Its chemical name is 5β,20-epoxy-1,2α,4,7β,10β,13α-hexahydroxytaxane-11-ene-9-one-4,10-diacetate-2-benzoate-13[(2'R,3'S)—N-benzoyl-3-phenylisoserine ester]. The structural formula is as follows:

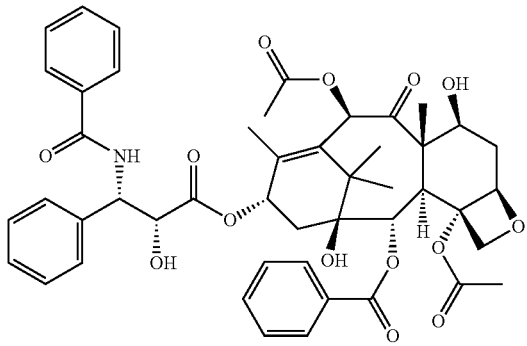 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

As a new type of anti-microtubule drug, paclitaxel maintains the stability of microtubules and inhibits cell mitosis by promoting the assembly of microtubules while inhibiting depolymerization of the same. Experiment in vitro shows that paclitaxel has a remarkable radiosensitization effect, and can arrest cells in G2 and M phases during which the cells are sensitive to radiotherapy. Paclitaxel is internationally recognized as the first choice of anticancer drug due to its unique mechanism of stabilizing cell microtubules, good therapeutic effect, broad spectrum and few side effects. At present, paclitaxel is widely used in the treatment of various malignant tumors, such as ovarian cancer, cervical cancer, breast cancer, lung cancer, laryngeal cancer and esophageal cancer.

Currently, the most commonly used paclitaxel injections in clinic mainly include, for example, Taxol® of Bristol-Myers Squibb company, Anzatax® of Faulding company, and domestic Paclitaxel® and Taxol®, etc. All of them are prepared by dissolving paclitaxel in a mixed solvent medium of 50:50 (v/v) polyoxyethylene castor oil (Cremophor EL) and dehydrated alcohol to make a 6 mg/ml paclitaxel injection. However, every above-mentioned commercial product contains a large amount of Cremophor EL, which would cause in vivo histamine release, resulting in serious allergic reactions such as drug-induced rash, tachypnea, bronchospasm, hypotension and the like in some patients after administration. In view of this, corticosteroids or antihistamines such as dexamethasone and aminophylline are currently used before the administration to prevent allergic reactions. Even so, severe allergic reactions still occur at above 2% and even cause death. In addition, Cremophor EL in these paclitaxel injections may leach out a large amount of plasticizer diethylethyl phthalate upon contacting with polyvinyl chloride plastic pipes and infusion bags, thus causing toxicity. In addition, the product is extremely unstable after dilution, and granular precipitates would form upon standing for more than 24 hours, which brings about great risks in clinical use. These problems severely limit the application of paclitaxel injection products.

Therefore, only a small amount of paclitaxel preparations are approved for clinical use, such as Abraxane® (paclitaxel albumin nanoparticle suspension for injection), Lipusu® (paclitaxel liposome for injection) and Genexolo-Paclitaxel® (paclitaxel-polylactic acid polyethylene glycol micelle for injection). Nevertheless, the application of these intravenous administrated injections needs to be carried out under the medical supervision of the hospital, which brings inconvenience to the patients. Therefore, oral solid preparation with flexible administration, low price and high compliance of patients, is obviously more advantageous.

Nevertheless, the development of paclitaxel pharmaceutical compositions suitable for oral solid preparation is still slow due to the low water solubility of paclitaxel. As paclitaxel has a pKa of 11.99, its solubility in water is lower than about 10 μg/ml (reported as 0.1~<10 μg/ml), and the lack of functional salt-forming groups in paclitaxel structure makes it impossible to improve solubility by being prepared as salt. Moreover, due to the effluxing function of the efflux protein P-glycoprotein (P-gp) in gastrointestinal mucosal cells, the amount of paclitaxel absorbed into the blood is reduced, resulting in a further decrease in the oral bioavailability of paclitaxel (about 2%).

Therefore, it is desirable to develop a new paclitaxel pharmaceutical composition and an oral solid preparation thereof.

SUMMARY

In one aspect, provided is a paclitaxel pharmaceutical composition, comprising paclitaxel as active ingredient and hydroxypropyl methylcellulose derivative as carrier material.

In another aspect, provided is also a pharmaceutical preparation, comprising the paclitaxel pharmaceutical composition according to the invention and pharmaceutically acceptable excipients. The pharmaceutical preparation is in the form of oral solid preparation, such as powder, granule, pill, capsule or tablet.

In another aspect, provided is also a process for preparing the paclitaxel pharmaceutical composition and the pharmaceutical preparation thereof, for example comprising but not limited to hot-melt extrusion and spray drying.

In another aspect, provided is use of the paclitaxel pharmaceutical composition or the pharmaceutical preparation thereof in the manufacture of a medicament for the prevention and treatment of malignant tumors and related diseases.

In another aspect, provided is also a method for the prevention and treatment of malignant tumors and related diseases, comprising administrating a subject in need thereof the paclitaxel pharmaceutical composition according to the invention or pharmaceutical preparation thereof.

In another aspect, provided is also the paclitaxel pharmaceutical composition according to the invention or pharmaceutical preparation thereof for use in the prevention and treatment of malignant tumors and related diseases.

DETAILED DESCRIPTION OF THE INVENTION

Figure 1:
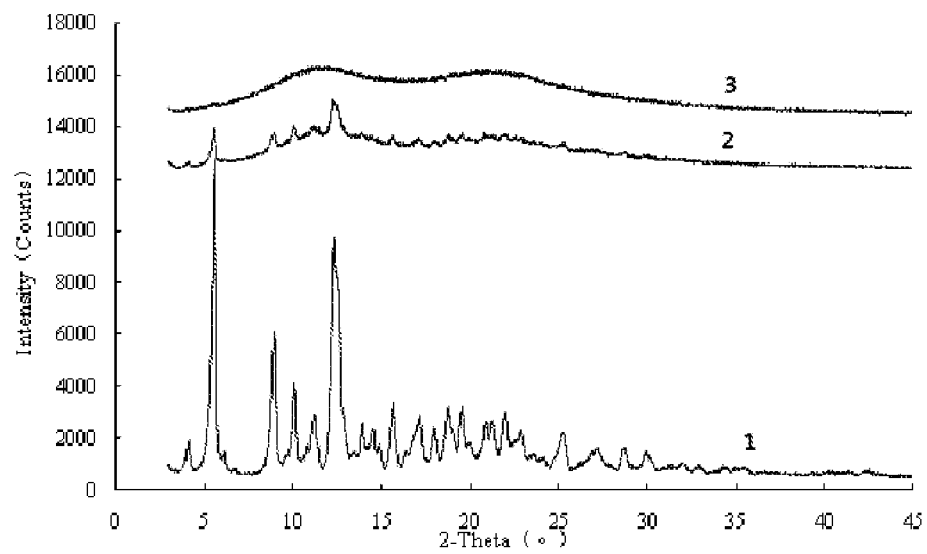
FIG. 1 shows the X-RD patterns of each product, wherein 1 represents paclitaxel as bulk drug substance, 2 represents physical mixture of paclitaxel-PVP K30-TPGS, and 3 represents comparative composition 1-1.

The invention will be further illustrated in details below. It should be understood that the description is intended for the purpose of illustration and is not intended to limit the invention.

Definition

Unless otherwise defined, the technical and scientific terms used herein have the same meanings as those commonly understood by one skilled in the art. In case of any contradiction, the definitions provided by the present application shall prevail. When an amount, concentration, or other value or parameter is expressed in the form of a range, a preferred range, or a preferred numerical upper limit or a preferred numerical lower limit, it should be understood that it equals to specifically disclosing any range as formed by combining any upper limit of a range or preferred value with any lower limit of a range or preferred value, regardless of whether the said range is specifically disclosed. Unless otherwise indicated, the numerical range listed herein encompasses the end points of the range and all integers and fractions (decimals) within that range.

The term "about", "approximately" when used in conjunction with the numerical variable, generally means that the value of the variable and all the values of the variable are within the experimental error (e.g., within a 95% confidence interval for the mean) or within a specified value±10% or within a broader range.

The term "stoichiometric ratio" refers preparation of various substances according to a certain weight ratios. For example, in the invention, paclitaxel as active ingredient and hydroxypropyl methylcellulose derivative as carrier material, optional polyethylene glycol 1000 vitamin E succinate (TPGS) are prepared in a specific proportion by weight.

The term "pharmaceutically acceptable" refers to contact with a patient's tissue within a normal range of medical judgment, having a reasonable benefit/risk ratio and is effective for target use without undue toxicity, irritation, allergic reaction, etc.

The term "dispersed in amorphous form" means that the drug is substantially dispersed in the carrier material in amorphous form to generate a single phase-forming material. For example, the drug may exist completely in amorphous state, i.e., there is no obvious crystal diffraction characteristic peak in powder X-ray diffraction detection. In the invention, this term refers to that paclitaxel as active ingredient completely disperses in hydroxypropyl methylcellulose derivative as carrier material in amorphous form to generate a single phase-forming pharmaceutical composition (solid dispersion or solid solution).

The terms "dissolved in", "dispersed in amorphous state", "solid dispersion", and "solid solution" cover any and all of these forms in the invention. These terms are conveniently used herein to describe the pharmaceutical composition according to the invention at various stages of preparation and at various temperatures.

The terms "pharmaceutical preparation", "pharmaceutical preparation product", "pharmaceutical dosage form", "dosage form", etc. refer to a drug administered to a patient in need of treatment, which may be in solid or liquid form, etc., such as powder, granule, pill, capsule, tablet, solution or suspension, patch, etc.

The term "pharmaceutical composition" refers to drug-carrying compositions comprising paclitaxel as active ingredient, hydroxypropyl methylcellulose derivative as carrier material, and optional TPGS in the form of solid dispersion.

The term "blank composition" refers to a composition in the form of solid dispersion that does not contain the active ingredient (i.e., paclitaxel), but comprises other components, compared with the corresponding pharmaceutical composition.

The term "physical mixture" refers to a mixture made of paclitaxel as active ingredient and hydroxypropyl methylcellulose derivative as the carrier material and optional TPGS by physical mixing only.

The term "peak time of plasma drug concentration ($T_{max}$)" refers to the average time to reach the maximum plasma drug concentration ($C_{max}$) of the drug after administration.

The term "peak plasma drug concentration ($C_{max}$)" refers to the peak drug concentration in plasma after drug administration.

The term "$AUC_{0-\infty}$" refers to average integrated area under curve of the plasma drug concentration over time from 0 to Go after drug administration.

The term "$AUC_{0-t}$" refers to average integrated area under curve of the plasma drug concentration over time from 0 to t after drug administration.

The term "average plasma drug concentration ($C_{ave}$)" refers to average plasma drug concentration obtained from the average integrated area under curve of the plasma drug concentration over time from 0 to t after drug administration ($AUC_{0-t}$) divided by release time t.

The term "plasma drug concentration fluctuation" refers to ratio of the peak plasma drug concentration ($C_{max}$) to the average plasma drug concentration ($C_{ave}$). The preferred $C_{max}/C_{ave}$ is 3 or less. Such ratio provides an average concentration within the treatment window while avoiding harmful drug side effects caused by higher ratio.

The term "bioavailability (BA)" refers to the extent to which a drug or therapeutically active substance may be utilized by a target tissue after administration. The bioavailability of the pharmaceutical preparation generally refers to a ratio of the area under the concentration-time curve (AUC) of the test formulation (T) administered through a non-vascular route (e.g., oral, p.o.) to the reference formulation (R) of the drug, through e.g., intravenous injection (i.v.) or the same route (p.o.), expressed as absorbance percentage. According to the similarities and differences between the administration routes of the test reagent and the reference reagent, it can be divided into absolute BA and relative BA. In addition, considering the possible difference of the dose (D), the calculation formulae are as follows:

$$\text{Absolute bioavailability(absolute BA)} = AUC_{po} \times D_{iv}/AUC_{iv} \times D_{po} \times 100\%.$$

$$\text{Relative bioavailability(relative BA)} = AUC_T \times D_R/AUC_R \times D_T \times 100\%.$$

The AUC in the above formulae refer to $AUC_{0-t}$, i.e. the average integrated area under curve of the plasma drug concentration over time from 0 to t after drug administration.

A Pharmaceutical Composition and a Pharmaceutical Preparation Thereof and Preparation Thereof Provided is a paclitaxel pharmaceutical composition comprising paclitaxel as active ingredient and hydroxypropyl methylcellulose derivative as carrier material.

In an embodiment of the invention, hydroxypropyl methylcellulose derivative as carrier material is one or more selected from the group consisting of hydroxypropyl methylcellulose acetate succinate (HPMCAS), hydroxypropyl methylcellulose phthalate (HPMCP), hydroxypropyl methylcellulose succinate (HPMCS), hydroxypropyl methylcellulose trimellitate (HPMCT), hydroxypropyl methylcellulose acetate phthalate (HPMCAP), and hydroxypropyl methylcellulose acetate maleate (HPMCAM).

In a preferable embodiment of the invention, hydroxypropyl methylcellulose derivative as carrier material is one or more selected from the group consisting of HPMCAS, HPMCT and HPMCAM. In a more preferable embodiment of the invention, hydroxypropyl methylcellulose derivative as carrier material is selected from the group consisting of HPMCAS.

In a preferable embodiment of the invention, hydroxypropyl methylcellulose derivative as carrier material is selected from at least one of HPMCAS having the following acetyl content and succinyl content:
(i) HPMCAS having an average acetyl content of 5 to 9 wt % and an average succinyl content of 14 to 18 wt % based on the total weight of HPMCAS;
(ii) HPMCAS having an average acetyl content of 7 to 11 wt % and an average succinyl content of 10 to 14 wt % based on the total weight of HPMCAS;
(iii) HPMCAS having an average acetyl content of 10 to 14 wt % and an average succinyl content of 4 to 8 wt % based on the total weight of HPMCAS.

In a particularly preferable embodiment of the invention, hydroxypropyl methylcellulose derivative as carrier material is selected from HPMCAS having an average acetyl content of 7-11 wt % and an average succinyl content of 10-14 wt %, based on the total weight of HPMCAS.

More specifically, in a very particularly preferable embodiment of the invention, hydroxypropyl methylcellulose derivative(s) as carrier material can be selected from, but are not limited to, for example, one or more commercial products of AQOAT® AS-L, AQOAT® AS-M and AQOAT® AS-H of Shin-Etsu company, as well as AquaSolve L, AquaSolve LM, AquaSolve LH and AquaSolve AS™ L, AquaSolve AS™ M, AquaSolve AS™ H of Ashland company.

In a very particularly preferable embodiment of the invention, hydroxypropyl methylcellulose derivative as carrier material is selected from the group consisting of AQOAT® AS-M.

In an embodiment of the invention, the weight ratio of paclitaxel as active ingredient and hydroxypropyl methylcellulose derivative as carrier material is about 1:1 to about 1:10, preferably about 1:1 to about 1:5, more preferably about 1:1 to 1:3, for example including but not limited to 1:1, 1:2, 1:3, 1:4, 1:5, 1:6, 1:7, 1:8, 1:9, 1:10, etc.

In addition, in another embodiment of the invention, the paclitaxel pharmaceutical composition may further comprise polyethylene glycol 1000 vitamin E succinate (D-α-tocopherol polyethylene glycol 1000 succinate, also known as TPGS, Vitamin E TPGS, or Tocophersolan). TPGS is a water-soluble derivative of vitamin E, which is formed by esterification of vitamin E succinate (VES) and polyethylene glycol (PEG) 1000, and has a relative molecular weight of about 1513, and has been recorded in the U.S. pharmacopeia. TPGS acts as a solubilizer in the pharmaceutical composition according to the invention and can further improve oral bioavailability by influencing the efflux of drugs.

In another embodiment of the invention, TPGS can be, for example, the commercial product Kolliphor® TPGS purchased from BASF company, but is not limited thereto.

In another embodiment of the invention, TPGS is Kolliphor® TPGS.

The amount of TPGS used in paclitaxel pharmaceutical composition according to the invention is not particularly limited and can be adjusted according to the practical situation. In general, the amount of TPGS is about 1 to 20 wt %, preferably 5 to 15 wt %, more preferably 5 to 10 wt %, even more preferably 10 to 15 wt %, for example, including but not limited to 5 wt %, 8 wt %, 10 wt %, 12 wt %, 15 wt %, 20 wt %, etc., based on the total weight of paclitaxel as active ingredient and hydroxypropyl methylcellulose derivative as carrier material.

In addition, provided is also a pharmaceutical preparation comprising paclitaxel pharmaceutical composition according to the invention.

In another embodiment of the invention, in addition to the above-mentioned pharmaceutical composition, paclitaxel pharmaceutical preparation according to the invention can also comprise additional pharmaceutically acceptable excipient(s).

In another embodiment of the invention, the pharmaceutically acceptable excipients include but not limited to one or more of surfactant, pH adjusting agent, diluent, disintegrant, binder, and lubricant.

In another embodiment of the invention, surfactant may be anionic, cationic, zwitterionic, or nonionic surfactant or mixtures thereof. In another preferable embodiment of the invention, surfactant is zwitterionic or nonionic surfactant or mixture thereof. In yet another more preferable embodiment of the invention, the surfactant is a mixture of two or more surfactants.

Surfactant can be selected according to the specific components and composition of the pharmaceutical preparation according to the invention.

In another preferable embodiment of the invention, surfactant suitable for the invention can be one or more selected from the following substances:

Polyoxyethylene castor oil derivative(s), such as polyoxyethylene glycerol triricinoleate, polyoxyethylene ether 35 castor oil (Cremophor EL, BASF).

Polyoxyethylene glyceryl stearate.

Polyethylene glycol castor oil derivative(s), such as polyethylene glycol 40 hydrogenated castor oil (Cremophor RH40) or polyethylene glycol 60 hydrogenated castor oil (Cremophor RH 60).

Block copolymer of epoxyethane and epoxypropane, also known as polyoxyethylene polyoxypropylene block copolymers or polyoxyethylene polypropylene glycol, such as Poloxamer 124, Poloxamer 188, Poloxamer 237, Poloxamer 388 or Poloxamer 407 (BASF).

Mono fatty acid esters of polyoxyethylene(20) sorbitan, such as polyoxyethylene(20) sorbitan monooleate (Tween 80), polyoxyethylene(20) sorbitan monostearate (Tween 60), polyoxyethylene(20) sorbitan monopalmitate (Tween 40), polyoxyethylene(20) sorbitan monolaurate (Tween 20).

Fatty acid esters of polyethylene glycol, such as PEG-200 monolaurate, PEG-200 dilaurate, PEG-300 dilaurate, PEG-400 dilaurate, PEG-300 distearate or PET-300 dioleate.

Fatty acid monoesters of alkylene glycol, such as propylene glycol monolaurate.

Sorbitan fatty acid monoesters such as sorbitan monolaurate (Span 20), sorbitan monooleate, sorbitan monopalmitate (Span 40) or sorbitan stearate.

In another preferable embodiment of the invention, the surfactant suitable for the invention is one or more of polyoxyethylene castor oil derivative(s), block copolymer of epoxyethane and epoxypropane, particularly preferably Cremophor RH40 and/or Poloxamer 188.

In another embodiment of the invention, the pH adjusting agent suitable for the invention can be one or more selected from the group consisting of citric acid, acetic acid, fumaric acid, maleic acid, tartaric acid, malic acid, succinic acid, oxalic acid, malonic acid, benzoic acid, mandelic acid and ascorbic acid, preferably citric acid.

In another embodiment of the invention, the diluent suitable for the invention can be one or more selected from the group consisting of microcrystalline cellulose, starch, pregelatinized starch, lactose, mannitol, calcium hydrophosphate.

In another embodiment of the invention, the disintegrant suitable for the invention can be one or more selected from the group consisting of carboxymethylcellulose, sodium carboxymethylcellulose, sodium croscarmellose, calcium carboxymethylcellulose, sodium carboxymethyl starch, crosslinked polyvinylpyrrolidone (i.e., crospovidone), low-substituted hydroxypropylcellulose (L-HPC), and hydroxymethyl starch.

In another embodiment of the invention, the binder suitable for the invention can be one or more selected from the group consisting of sodium carboxymethylcellulose, hydroxypropylcellulose, methylcellulose, ethylcellulose, or hypromellose.

In another embodiment of the invention, the lubricant suitable for the invention can be one or more selected from the group consisting of magnesium stearate, silica, talc, stearic acid, and hydrogenated vegetable oil.

It should be noted that the pharmaceutically acceptable excipients listed above are only illustrative and representative. Therefore, the pharmaceutical preparation of the invention is not limited to the pharmaceutically acceptable excipients listed above. A person skilled in the art can make various changes, modifications or equivalent replacements to the above excipients according to conventional technologies, without exceeding the protection scope of the invention.

In an embodiment of the invention, the pharmaceutical preparation is an oral solid preparation. For example in the form of powder, granule, pills, capsule or tablet.

Provided is also a process for preparing the paclitaxel pharmaceutical composition, comprising but not limited to hot-melt extrusion and spray drying.

In an embodiment of the invention, hot-melt extrusion is applied to prepare the paclitaxel pharmaceutical composition. The process comprises the following steps:

Feeding the paclitaxel as active ingredient, hydroxypropyl methylcellulose derivative as carrier material and optional TPGS in stoichiometric ratio into a hot-melt extruder preheated to about 120° C. to about 180° C.;

and cooling the extruded mixture, pulverizing and sieving to obtain the paclitaxel pharmaceutical composition of the invention.

In another embodiment of the invention, hot-melt extrusion is applied to prepare the paclitaxel pharmaceutical composition, but there is no particular restriction on the feeding sequence, as long as the target product of the invention can be obtained.

In a preferable embodiment of the invention, hot-melt extrusion is applied to prepare the paclitaxel pharmaceutical composition, wherein paclitaxel, hydroxypropyl methylcellulose derivative as carrier material and optional TPGS are mixed in stoichiometric ratio prior to feeding; or the above components are fed directly without being mixed beforehand.

In another embodiment of the invention, there is no particular restriction on the cooling method. It may include air cooling, water cooling, mechanical cooling, etc.

The type of extruder suitable for the process of the invention is also not particularly restricted, and it includes but not limited to single-screw or twin-screw hot-melt extruder.

In an embodiment of the invention, a twin-screw extruder is applied to prepare the paclitaxel pharmaceutical composition. In this case, there is no particular restriction on the type of screw rotation, and it includes but not limited to co-rotating, counter-rotating, and biconical screw rotation modes.

In a preferable embodiment of the invention, a co-rotating twin-screw extruder is applied to prepare the paclitaxel pharmaceutical composition of the invention.

In a preferable embodiment of the invention, the melting temperature of the hot-melt extruder is set to be about 120 to about 190° C., preferably 120 to 180° C., preferably 120 to 170° C., more preferably 120 to 160° C., even more preferably 120 to 150° C., most preferably 140° C., for example include but not limited to 120° C., 130° C., 140° C., 150° C., 160° C., 170° C. and 180° C., etc.

In another preferable embodiment of the invention, the rotation speed of the screw is about 50 to about 500 rpm, preferably 100 to 500 rpm, more preferably 150 to 500 rpm, even more preferably 150 to 200 rpm, most preferably 150 rpm, for example include but not limited to 50 rpm, 100 rpm, 150 rpm, 200 rpm, 250 rpm, 300 rpm, 350 rpm, 400 rpm, 450 rpm, 500 rpm, etc.

In another preferable embodiment of the invention, the ratio of the length to diameter of the screw (L/D) is about 15 to about 40, preferably about 15 to about 35, more preferably about 15 to about 30, even more preferably about 15 to about 25, most preferably about 20 to about 30, most preferably about 25, for example include but not limited to 15, 18, 20, 25, 30, 35, 40, etc.

If the melting temperature is too low, the L/D is too short, the rotation speed of the screw is too slow, the thermal energy and mechanical energy provided in the hot melting process would be insufficient, thus causing paclitaxel, hydroxypropyl methylcellulose derivative(s) as carrier material and optional TPGS unable to form a melted state, and consequently paclitaxel is unable to be dispersed uniformly in the melted hydroxypropyl methylcellulose derivative(s) as carrier material. Although paclitaxel is fully mixed with hydroxypropyl methylcellulose derivative(s) as carrier material, due to the low melting temperature, a single phase-forming solid dispersion (solid solution) that is completely dispersed in amorphous state cannot be obtained.

Nevertheless, if the melting temperature is too high, the L/D is too long, or the screw rotation speed is too fast, the thermal energy and mechanical energy provided in the hot-melt process would be excessive. Even if a single phase-forming solid dispersion completely dispersed in amorphous state is obtained, there would be unnecessary degradation of paclitaxel, hydroxypropyl methylcellulose derivative(s) as carrier material and optional TPGS.

Therefore, it is quite necessary to select melting temperature, screw rotation speed and the ratio of the length to the diameter of the screw of the hot-melt extruder suitable for the process of the invention.

As shown by the experiments, in the paclitaxel pharmaceutical composition prepared according to the process of the invention, paclitaxel is completely dispersed or dissolved in amorphous state in the hydroxypropyl methylcellulose derivative as carrier material.

If desired, the paclitaxel pharmaceutical composition according to the invention can be mixed with pharmaceutically acceptable excipient(s), and prepared into various types of oral solid preparation using specific equipment, for example, tablet can be prepared by tableting using a single punch tablet machine (Shanghai Tianfan Pharmaceutical Machinery Factory, type DP-5). Or it may be prepared into powder, granule, pill or capsule by other equipment to facilitate clinical application.

Provided is also use of the paclitaxel pharmaceutical composition and the pharmaceutical preparation thereof in the manufacture of a medicament for the prevention and treatment of malignant tumors and related diseases.

Beneficial Effects

Compared with the prior art, the preparation process of the pharmaceutical composition according to the invention and the pharmaceutical preparation thereof is simple and easy to operate, especially the hot-melt extrusion process. The product is easy to grind, has good compressibility, good reproducibility and can be produced on a large scale, and experiments show that paclitaxel is completely dispersed in amorphous state in hydroxypropyl methylcellulose derivative as carrier material in the pharmaceutical composition obtained by the process.

The inventor also unexpectedly find that the solubility and in vitro dissolution of the pharmaceutical compositions comprising paclitaxel as active ingredient and hydroxypropyl methylcellulose derivative(s) as carrier material according to the invention are significantly improved, compared with the paclitaxel as bulk drug substance and the corresponding compositions in comparative Example 1. When TPGS is further added, the solubility and in vitro dissolution of the obtained pharmaceutical composition are further enhanced. It is indicated that the carrier material HPMCAS and TPGS have synergistic solubilization effect on pharmaceutical compositions.

In another aspect, the inventor also find that compared with the paclitaxel as bulk drug substance and the corresponding comparative preparation ORAXOL™, the in vivo bioavailability of the pharmaceutical composition according to the invention is significantly improved. Compared with the comparative preparation ORAXOL™, the same clinical therapeutic effect is achieved with only a lower dose of active ingredient, thus the side effects can be reduced and the medication cost can be decreased.

EXAMPLES

The technical solution of the invention is hereinafter further illustrated by specific examples. It should be noted that the examples are merely exemplary and cannot be interpreted as restricting the protection scope of the invention. The invention may also have other embodiments, or can be practiced or carried out in various ways.

Unless otherwise specified, all percentages, parts, proportions and the like are calculated on the basis of weight.

Process for Evaluating and Determining Physicochemical Properties of the Paclitaxel Pharmaceutical Composition Powder X-ray diffraction (X-RD): an appropriate amount of bulk drug substance of paclitaxel, physical mixture, comparative composition or the pharmaceutical composition of the invention are weighted respectively. The powder X-ray diffraction patterns are recorded under the conditions of Cu target, 45 kv voltage and 45 mA current (D8ADVANCE X-ray diffractometer manufactured by BRUKER).

Apparent solubility determination: an excessive amount of the pharmaceutical compositions was weighed and put into a container. Phosphate buffer solution with pH6.8 was added respectively. The volume of the phosphate buffer solution was about 2/3 of volume of the container. The container was then shaken in a shaking table at 37° C. for 3 h. The resulting solution was filtered with a 0.45 µm filter membrane, then the filtrate was collected, further diluted with an appropriate amount of methanol, mixed by vortex and analyzed by HPLC.

Wherein the HPLC analysis parameters are as follows:

| | |
|---|---|
| Chromatographic column | Phenyl column (3.5 µm, 4.6 × 100 mm) |
| Mobile phase | Methanol:water (70:30, v/v) |
| Flow rate | 0.8 ml/min |
| Sample plate | 25° C. |
| Detection wavelength | 227 nm |
| Injection amount | 10 µl |

Dissolution Determination:

| | |
|---|---|
| Dissolution method | USP II method (slurry method) |
| Dissolution medium | pH 6.8 buffer + 0.2% Tween 80 |
| Rotation speed | 100 rpm |
| Temperature | 37.5° C. |
| Test dose | 100 mg (paclitaxel)/cup |
| Sampling time | 15, 30, 45, 60, 120 min |

Wherein pH6.8 represents the environment simulating the human intestinal tract (small intestine).

Analysis of dissolved sample: the solution obtained in the dissolution determination test was filtered with a 0.45 µm filter membrane, then the filtrate was collected, further diluted with an appropriate amount of methanol, mixed by vortex and analyzed by HPLC. The HPLC analysis method of the dissolved sample was the same as the HPLC analysis method mentioned above in the solubility determination.

Comparative Example 1 Paclitaxel-PVP K30 Pharmaceutical Composition (not the Present Invention)

1. Preparation
1) Composition:
The specific composition of paclitaxel-PVP K30 pharmaceutical composition/physical mixture is shown in Table 1-1.
2) Preparation:
Paclitaxel-PVP K30 pharmaceutical composition: according to the specific composition and amount in Table 1-1, paclitaxel and the carrier material PVP K30 (purchased from BASF, trade name Kollidon 30®) and optional Kolliphor® TPGS were respectively added into a mixer and mixed uniformly, and then fed into a hopper of a co-rotating twin screw extruder (Omicron 12 of Steer Corporation, India); or according to the composition and amount in Table 1-1, the above components were directly fed into the hopper of the co-rotating twin screw extruder. The melting temperature of the co-rotating twin screw extruder was controlled to be about 190° C., and the screw rotation speed was about 150 rpm. Then, the extruded extrudate was cooled, pulverized and sieved to obtain solid powder, namely paclitaxel-PVP K30 pharmaceutical composition (abbreviated as comparative compositions 1-1, 1-2).

Paclitaxel-PVP K30 physical mixture: according to the specific composition and amount in Table 1-1, the active ingredient paclitaxel and the carrier material PVP K30 (purchased from BASF, trade name Kollidon 30®) and optional Kolliphor® TPGS were physically mixed uniformly to obtain the corresponding paclitaxel-PVP K30 physical mixture.

If desired, pharmaceutical composition/physical mixture obtained as above is mixed uniformly with the pharmaceutical excipients in Table 1-2 and formulated to obtain the corresponding pharmaceutical preparation.

TABLE 1-1

Specific composition (parts by weight) of paclitaxel-PVP K30 pharmaceutical composition/physical mixture

| Component | Function | Comparative composition 1-1 | Comparative composition 1-2 |
|---|---|---|---|
| Paclitaxel | Active ingredient | 11.3 | 11.3 |
| PVP K30 | Carrier material | 33.9 | 33.9 |
| Kolliphor ® TPGS | Solubilizer | 4.5 | / |

TABLE 1-2

Excipients for paclitaxel-PVP K30 pharmaceutical composition/physical mixture (parts by weight)

| Component | Function | Comparative composition 1-1 | Comparative composition 1-2 |
|---|---|---|---|
| Microcrystalline cellulose | Diluent | 31.1 | 35.6 |
| Crospovidone | Disintegrant | 18.6 | 18.6 |
| Silica | Lubricant | 0.4 | 0.4 |
| Magnesium stearate | Lubricant | 0.2 | 0.2 |

2. Evaluation of physical and chemical properties
1) Powder X-ray diffraction (X-RD) detection:
Powder X-ray diffraction (X-RD) was used to further confirm the dispersed state/crystal structure of the active ingredient paclitaxel in the bulk drug substance/pharmaceutical composition/physical mixture.

As can be seen from FIG. 1, the bulk drug substance of paclitaxel has obvious crystal diffraction characteristic peaks. Physical mixture comprising paclitaxel, the carrier material PVP K30 and TPGS also has some crystal diffraction characteristic peaks of paclitaxel, which indicates that some paclitaxel in the physical mixture exists in crystal state. Nevertheless, in the pharmaceutical composition comprising paclitaxel, the carrier material PVP K30 and TPGS (i.e., comparative composition 1-1), the crystalline characteristic peak of paclitaxel disappears, indicating that paclitaxel is completely dispersed in amorphous state in the pharmaceutical composition.

The experiment also shows that the physical mixture comprising only paclitaxel and the carrier material PVP K30 still has some crystal diffraction characteristic peaks, which indicates that some paclitaxel in the physical mixture exists in crystal state; while the pharmaceutical composition comprising paclitaxel and the carrier material PVP K30 (i.e., comparative composition 1-2) has lost the characteristic peaks of paclitaxel crystal, indicating that paclitaxel is completely dispersed in amorphous state in the pharmaceutical composition in the composition.

2) Apparent Solubility Determination
The apparent solubility of the bulk drug substance of paclitaxel and comparative compositions 1-1 and 1-2 were determined according to the process described above. The results are shown in Table 1-3 below.

TABLE 1-3

Apparent solubility in pH 6.8 phosphate buffer

| | Bulk drug | Comparative composition 1-1 | Comparative composition 1-2 |
|---|---|---|---|
| Solubility (µg/ml) | 4.0 | 87.9 | 25.6 |
| Ratio of solubility (composition/bulk drug) | 1 | 22.0 | 6.4 |

As can be seen from Table 1-3, compared with the bulk drug substance of paclitaxel, the solubility of the pharmaceutical compositions comprising paclitaxel and the carrier material PVP K30 (i.e., comparative composition 1-2) has increased by a certain extent. When Kolliphor® TPGS is further added, the solubility of the pharmaceutical composition (i.e., comparative composition 1-1) has significantly increased, indicating that the carrier material PVP K30 and Kolliphor® TPGS have synergistic solubilization effect on the pharmaceutical composition.

3) Determination of Dissolution

The dissolution of the bulk drug substance of paclitaxel and the comparative compositions 1-1 and 1-2 were determined according to the above process. The results are shown in Table 1-4 below.

TABLE 1-4

Dissolution in medium conversion at pH6.8

| | Dissolution % | | | | |
|---|---|---|---|---|---|
| | 15 min | 30 min | 45 min | 60 min | 120 min |
| Bulk drug | 13.1 | 14.5 | 14.6 | 14.8 | 14.1 |
| Comparative composition 1-1 | 43.5 | 52.7 | 53.4 | 52.9 | 48.0 |
| Comparative composition 1-2 | 22.6 | 31.8 | 32.5 | 33.6 | 31.9 |

As can be seen from Table 1-4, the dissolution of the bulk drug substance at pH6.8 is very low, only 14.8% at 60 min, while the dissolution of the pharmaceutical composition comprising paclitaxel and PVP K30 (i.e., comparative composition 1-2) increases to 33.6% at 60 min. After further addition of Kolliphor® TPGS, the dissolution of the pharmaceutical composition (i.e., comparative composition 1-1) increases to 52.9% at 60 min. It is indicated that the carrier materials PVP K30 and Kolliphor® TPGS have synergistic solubilization effect on pharmaceutical compositions.

Example 1 Paclitaxel-HPMCAS Pharmaceutical Composition/Physical Mixture (the Present Invention)

1. Preparation
1) Composition:

The specific composition of paclitaxel-HPMCAS pharmaceutical composition/physical mixture is shown in Table 2-1.

2) Preparation:

Paclitaxel-HPMCAS pharmaceutical composition: according to the specific composition and amount in Table 2-1, paclitaxel and the carrier material HPMCAS (specifically AQOAT® AS-M) and optional Kolliphor® TPGS were respectively added into a mixer and mixed uniformly, and then fed into a hopper of a co-rotating twin screw extruder (Omicron 12 of Steer Corporation, India); or according to the specific composition and amount in Table 2-1, the above components were directly fed into the hopper of the co-rotating twin screw extruder. The melting temperature of the co-rotating twin-screw extruder was set to about 140° C. and the rotation speed of the screw was about 150 rpm. The extruded extrudate was cooled, pulverized and sieved to obtain solid powder, namely paclitaxel-HPMCAS pharmaceutical composition of the invention (abbreviated as composition, such as composition 2-1, composition 2-4, etc.).

Physical mixture: the active ingredient paclitaxel and the carrier material HPMCAS and optional Kolliphor®TPGS were physically mixed uniformly according to the specific composition and amount in Table 2-1 to obtain the corresponding physical mixture.

If desired, the pharmaceutical composition obtained above is mixed uniformly with the pharmaceutical excipients in Table 2-2 to obtain the corresponding pharmaceutical preparation. For example, tablet can be prepared by tableting using a single punch tablet machine (Shanghai Tianfan Pharmaceutical Machinery Factory, type DP-5). Or it may be prepared into powder, granule, pill or capsule by other equipment.

TABLE 2-1

Composition (parts by weight) of paclitaxel-HPMCAS pharmaceutical composition of the invention

| Component | Function | Composition 2-1 | Composition 2-2 | Composition 2-3 | Composition 2-4 | Composition 2-5 | Composition 2-6 |
|---|---|---|---|---|---|---|---|
| Paclitaxel | Active ingredient | 16.67 | 12.50 | 8.00 | 11.30 | 11.30 | 11.30 |
| AQOAT ® AS-M | Carrier material | 16.67 | 37.50 | 40.00 | 33.90 | 33.90 | 33.90 |
| Kolliphor ® TPGS | Solubilizer | / | / | / | 4.50 | 2.30 | 6.80 |

TABLE 2-2

Pharmaceutical excipients (parts by weight) of paclitaxel-HPMCAS pharmaceutical composition of the invention

| | | | | | | | |
|---|---|---|---|---|---|---|---|
| Microcrystalline cellulose | Diluent | 48.70 | 30.00 | 32.00 | 32.80 | 32.80 | 30.50 |
| Hydroxypropylcellulose | Binder | 10.50 | 12.50 | 12.50 | 10.00 | 12.20 | 10.00 |
| Sodium croscarmellose | Disintegrant | 6.66 | 6.70 | 6.70 | 6.70 | 6.70 | 6.70 |
| Silica | Lubricant | 0.50 | 0.50 | 0.50 | 0.50 | 0.50 | 0.50 |
| Magnesium stearate | Lubricant | 0.30 | 0.30 | 0.30 | 0.30 | 0.30 | 0.30 |

2. Evaluation of Physical and Chemical Properties
1) Powder X-Ray Diffraction (X-RD) Test:

Powder X-ray diffraction (XRD) was applied to further confirm the dispersed state/crystal structure of the active ingredient paclitaxel in the bulk drug substance/pharmaceutical composition/physical mixture.

Figure 2:
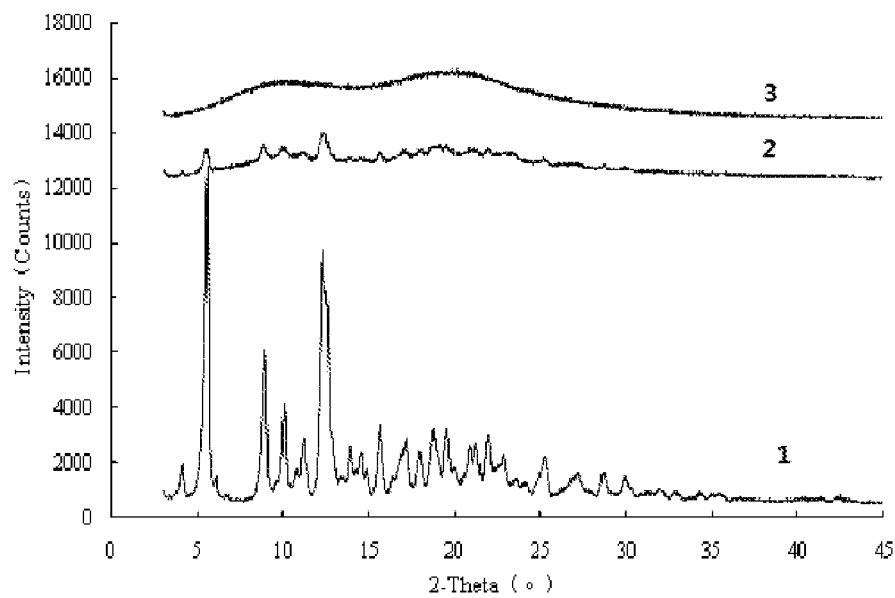
FIG. 2 shows the X-RD patterns of each product, wherein 1 represents paclitaxel as bulk drug substance, 2 represents physical mixture of paclitaxel-HPMCAS-TPGS, and 3 represents the pharmaceutical composition 2-4 according to the invention.

As can be seen from FIG. 2, the bulk drug substance of paclitaxel has obvious crystal diffraction characteristic peaks; physical mixture comprising paclitaxel, and the carrier material HPMCAS also still has some crystal diffraction characteristic peaks, which indicates that some paclitaxel in the physical mixture exists in crystal state. Nevertheless, in the pharmaceutical composition of the invention (for example, composition 2-4), the crystalline characteristic peak of paclitaxel disappears, indicating that paclitaxel is completely dispersed in amorphous state in the pharmaceutical composition.

The experiment also shows that the physical mixture comprising only paclitaxel and the carrier material HPMCAS still have some crystal diffraction peaks, which indicates that some paclitaxel in the physical mixture exists in crystal state; while the pharmaceutical compositions comprising paclitaxel and the carrier material HPMCAS (for example, compositions 2-2 and 2-3) have lost the characteristic peaks of paclitaxel crystals, which indicates that paclitaxel is completely dispersed in amorphous state in the pharmaceutical composition.

2) Apparent Solubility Determination

Apparent solubility of each composition was determined according to the above process. The results are shown in Table 2-3 below.

TABLE 2-3

Apparent solubility in phosphate buffer with pH 6.8

|  | Bulk drug | Composition 2-1 | Composition 2-2 | Composition 2-3 | Composition 2-4 |
|---|---|---|---|---|---|
| Solubility (µg/ml) | 4.0 | 39.7 | 53.6 | 81.5 | 110.4 |
| Ratio of solubility (composition/bulk drug) | 1 | 9.9 | 13.4 | 20.4 | 27.6 |

As can be seen from Table 2-3, compared with the bulk drug substance of paclitaxel and comparative Example 1, the solubility of pharmaceutical composition of the invention comprising paclitaxel and the carrier material HPMCAS (for example, composition 2-2) is obviously improved, which shows that the carrier material HPMCAS has solubilizing effect on paclitaxel and can obviously improve the solubility and dissolution of the bulk drug substance of paclitaxel. After further addition of Kolliphor® TPGS, the solubility of pharmaceutical composition (for example, composition 2-4) is greatly improved, and the solubilizing effect is more obvious, which shows that the carrier material HPMCAS and TPGS have synergistic solubilization effect on the pharmaceutical composition. In addition, when compared with comparative Example 1, the solubilization effect of the pharmaceutical composition of the invention is also obviously superior to the corresponding pharmaceutical composition of comparative Example 1.

3) Determination of Dissolution

The dissolution of each composition was determined according to the above process. The results are shown in Table 2-4 below.

TABLE 2-4

Dissolution in medium conversion at pH 6.8

| | Dissolution % | | | | |
|---|---|---|---|---|---|
| | 15 min | 30 min | 45 min | 60 min | 120 min |
| Bulk drug | 13.1 | 14.5 | 14.6 | 14.8 | 14.1 |
| Composition 2-1 | 22.3 | 28.6 | 33.2 | 38.7 | 38.6 |
| Composition 2-2 | 42.1 | 49.3 | 53.7 | 55.8 | 59.7 |
| Composition 2-3 | 50.9 | 58.7 | 66.3 | 72.7 | 73.9 |
| Composition 2-4 | 51.6 | 74.9 | 83.9 | 90.6 | 93.3 |
| Composition 2-5 | 43.6 | 61.8 | 69.5 | 78.5 | 81.1 |
| Composition 2-6 | 53.3 | 76.0 | 85.1 | 91.3 | 92.9 |

As can be seen from Table 2-4, the dissolution of the bulk drug substance of paclitaxel is very low at pH6.8, only 14.8% at 60 min, and the dissolution of the pharmaceutical composition 2-1 of the invention (paclitaxel:HPMCAS=1:1, weight ratio) at 60 min is about 38.7%, which is better; and with the increase of the carrier material HPMCAS, the dissolution of the composition 2-2 of the invention (paclitaxel:HPMCAS=1:3, weight ratio) and composition 2-3 (paclitaxel:HPMCAS=1:5, weight ratio) at 60 min increases to 55.8% and 72.7% respectively. After further adding the corresponding amount of Kolliphor® TPGS respectively on the basis of composition 2-2 (i.e., paclitaxel:HPMCAS=1:3, weight ratio), wherein the amount of TPGS is for example equivalent to 10%, 5% and 15% of the total weight of the bulk drug substance and the carrier material, it is surprisingly found that the obtained composition (e.g., composition 2-6) significantly increases the dissolution of the bulk drug substance of paclitaxel, e.g., the dissolution is up to 91.3% at 60 min. In particular, when Kolliphor® TPGS was added in an amount equivalent to 10% of the total weight of the bulk drug substance and the carrier material, the dissolution of the composition (e.g., composition 2-4) at 60 min is increased from 55.8% to 90.6%, and the dissolution at 120 min is increased from 59.7% to 93.3%.

Furthermore, it can be seen from Table 2-4 that the dissolution of the composition of the invention gradually increases from 15 min to 120 min, while the dissolution of the bulk drug substance of paclitaxel doesn't vary significantly during this period.

The above experiments show that the pharmaceutical composition of the invention can significantly improve the solubility and dissolution of paclitaxel compared with the bulk drug substance of paclitaxel and comparative Example 1. Especially when Kolliphor® TPGS is further added to the pharmaceutical composition of the invention, the dissolution of the pharmaceutical composition is greatly improved, which shows that the carrier materials HPMCAS and Kolliphor® TPGS have synergistic solubilization effect on the pharmaceutical composition.

Example 2 Pharmacokinetics of Paclitaxel-HPMCAS Pharmaceutical Composition of the Invention 1. Experimental Preparation Test Preparation:

Tablets of paclitaxel-HPMCAS composition 2-4 prepared according to Example 1. Comparative preparation:

ORAXOL™: paclitaxel oral liquid used in phase I clinical trials (clinical trial No. NCT01967043, ClinicalTrials.gov), wherein 30 mg paclitaxel is included in per ml of mixed solution of PEG and Tween 80.

2. Experimental Methods

Beagle dogs were randomly divided into two groups. The beagle dogs were subjected to a one-period, parallel study and fasted for 12 h before the study. Blank blood samples were collected before administration. ORAXOL™ and paclitaxel-HPMCAS composition 2-4 were administered orally at a dose of 15 mg/kg respectively, while 200 ml warm water was delivered. 3 ml of blood was collected from the forelegs vein and placed in heparin-coated test tubes, at 5 min before administration, and 0.5, 1.0, 2.0, 3.0, 4.0, 6.0, 8.0, 12.0 h after respective oral administration of ORAXOL™ and paclitaxel-HPMCAS composition 2-4, respectively. Then 2 ml was taken from the test tube and placed in a 10 ml centrifuge tube, and stored in a refrigerator at −20° C. for later use.

Figure 3:
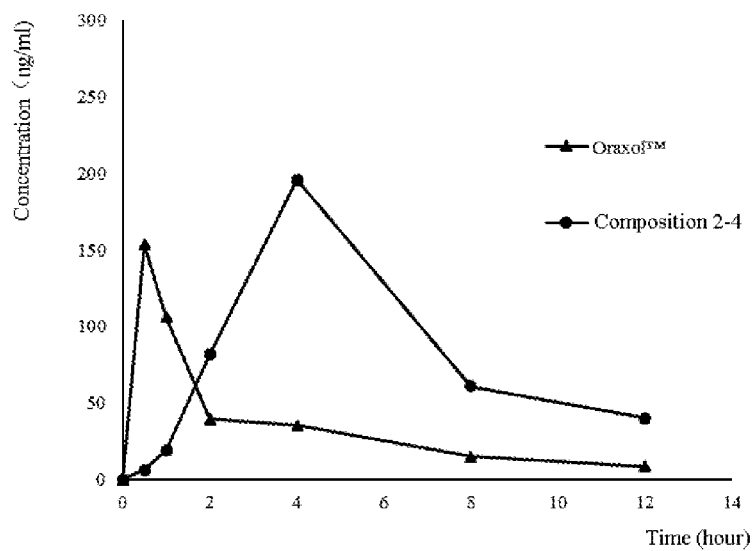
FIG. 3 is average plasma drug concentration-time curve of paclitaxel after administration of the pharmaceutical composition 2-4 according to the invention and ORAXOL™ to beagle dogs.

The concentration of paclitaxel in each plasma sample was determined by LC-MS/MS method. The bio-statistics was calculated and analyzed by pharmacokinetic statistics software DAS2.0. The test results are shown in FIG. 3 and Table 3-1.

TABLE 3-1

Main pharmacokinetic parameters of paclitaxel

| Pharmacokinetic parameters | ORAXOL™ | Composition 2-4 |
|---|---|---|
| Dosage form | Oral liquid | Tablet |
| Administration route | p.o. | p.o. |
| $C_{max}$ (ng/ml) | 179.88 | 225.00 |
| $AUC_{0-12\ h}$ (ng · h/ml) | 395.45 | 1050.65 |
| $T_{max}$ (h) | 0.5 | 4.0 |
| $t_{1/2}$ (h) | 3.4 | 5 |
| $C_{ave}$ | 32.95 | 87.55 |
| Relative bioavailability | — | 265.68 |

As can be seen from Table 3-1, compared with oral liquid ORAXOL™, the relative bioavailability of the pharmaceutical composition according to the invention is 265.68%, which shows that the pharmaceutical composition of the invention has significantly improved the bioavailability of paclitaxel.

In addition, as can be seen from FIG. 3, the plasma drug concentration fluctuation of the pharmaceutical composition according to the invention in vivo is smaller ($C_{max}/C_{ave}$=2.57), the absorption is milder, and maintaining time for the plasma drug concentration is longer. Similarly, it can also be found from FIG. 3 that the pharmaceutical composition of the invention can maintain a plasma drug concentration, which is higher than the average plasma drug concentration $C_{ave}$ of Oraxol™, for about 10 hours in vivo. Therefore, the pharmaceutical composition according to the invention greatly increases the absorption of paclitaxel in vivo and is more suitable for the treatment of diseases.

Although the invention has elaborated and described the typical embodiments, the invention is not limited to the details. Since various possible modifications and replacements do not depart from the spirit of the invention, a person skilled in the art is able to contemplate variations and equivalents of the invention by conventional tests, thus all of these variations and equivalents fall within the spirit and scope of the invention defined by the following claims.

The invention claimed is:

1. A paclitaxel pharmaceutical composition, comprising paclitaxel as active ingredient and hydroxypropyl methylcellulose derivative as carrier material, wherein, the hydroxypropyl methylcellulose derivative as carrier material is hydroxypropyl methylcellulose acetate succinate, the weight ratio of paclitaxel to hydroxypropyl methylcellulose derivative is 1:2-1:4, the pharmaceutical composition further comprises polyethylene glycol 1000 vitamin E succinate, and the amount of polyethylene glycol 1000 vitamin E succinate is 1% to 20 wt %, based on the total weight of the paclitaxel and the hydroxypropyl methylcellulose derivative as carrier material.

2. The paclitaxel pharmaceutical composition of claim 1, wherein,
the paclitaxel is completely dispersed in amorphous state in the hydroxypropyl methylcellulose derivative as carrier material.

3. An oral solid pharmaceutical preparation, comprising the paclitaxel pharmaceutical composition of claim 1.

4. The oral solid pharmaceutical preparation of claim 3, wherein,
the pharmaceutical preparation further comprises pharmaceutically acceptable excipient, wherein the excipient is one or more selected from the group consisting of surfactant, pH adjusting agent, diluent, disintegrant, binder, and lubricant.

5. A process for preparing the paclitaxel pharmaceutical composition of claim 1, comprising:
feeding the paclitaxel, the hydroxypropyl methylcellulose derivative as carrier material and optional polyethylene glycol 1000 vitamin E succinate in stoichiometric ratio directly into a hot-melt extruder preheated to 120° C. to 180° C., or
after uniform mixing, feeding the paclitaxel, the hydroxypropyl methylcellulose derivative as carrier material and optional polyethylene glycol 1000 vitamin E succinate in stoichiometric ratio into a hot-melt extruder preheated to 120° C. to 180° C.;
and
cooling the extruded mixture, pulverizing and sieving to obtain the paclitaxel pharmaceutical composition.

6. The process of claim 5, wherein,
the melting temperature of the hot-melt extruder is 120 to 180° C., the rotation speed of the screw is 50 to 500 rpm, the ratio of the length to diameter of the screw is 15-40.

7. The paclitaxel pharmaceutical composition of claim 1, wherein, the weight ratio of paclitaxel to hydroxypropyl methylcellulose derivative as carrier material is 1:3.

8. The paclitaxel pharmaceutical composition of claim 1, wherein,
the amount of polyethylene glycol 1000 vitamin E succinate is 5 to 15 wt %, based on the total weight of the paclitaxel and the hydroxypropyl methylcellulose derivative as carrier material.

9. An oral solid pharmaceutical preparation, comprising the paclitaxel pharmaceutical composition of claim 1, wherein the pharmaceutical preparation is in the form of powder, granule, pill, capsule or tablet.

* * * * *